(12) United States Patent
Assaker et al.

(10) Patent No.: US 8,016,864 B2
(45) Date of Patent: Sep. 13, 2011

(54) ANTERIOR IMPLANT FOR THE SPINE

(75) Inventors: Richard Assaker, Kain (BE);
Richard-Laurent Minfelde, Paris (FR);
Jean-Francois D'Amore, Montevrain (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 1188 days.

(21) Appl. No.: 11/734,140

(22) Filed: Apr. 11, 2007

(65) Prior Publication Data
US 2010/0069968 A1   Mar. 18, 2010

Related U.S. Application Data

(63) Continuation of application No. 10/693,604, filed on Oct. 27, 2003, now abandoned, which is a continuation of application No. 09/692,894, filed on Oct. 20, 2000, now Pat. No. 6,652,525, which is a continuation of application No. PCT/IB99/00794, filed on Apr. 30, 1999.

(30) Foreign Application Priority Data

Apr. 30, 1998   (FR) ..................... 98 05558

(51) Int. Cl.
*A61B 17/80*   (2006.01)

(52) U.S. Cl. ..................................................... 606/296
(58) Field of Classification Search ............... 606/70, 606/71, 280–299
See application file for complete search history.

(56) References Cited

U.S. PATENT DOCUMENTS

| 1,025,008 | A |   | 4/1912 | Miner |
| 2,406,832 | A | * | 9/1946 | Hardinge ........................ 606/71 |
| 2,443,363 | A | * | 6/1948 | Townsend et al. .............. 606/71 |

(Continued)

FOREIGN PATENT DOCUMENTS

CH                373516         11/1963

(Continued)

OTHER PUBLICATIONS

Cross Medical Products, Inc.'s Reply and Counterclaims to Medtronic's Counterclaims (Nov. 13, 2003), *Cross Medical Products, Inc.* v. *Medtronic Sofamor Danek, Inc. et al.*, No. SACV 8:03-0110 GLT (C.D. Cal. filed Feb. 4, 2003).

(Continued)

*Primary Examiner* — Eduardo C Robert
*Assistant Examiner* — Jerry Cumberledge (57) ABSTRACT

Implant for the cervical spine comprising an anterior plate (1) for maintaining a bone graft, bone anchorage screws (6,7,8) for the plate and means (22) for blocking the screws and preventing any migration of the screws, characterized in that the blocking means comprises at least one slide (22) slidably mounted on the plate so as to be applicable on at lease one anchorage screw head (15,16). The slide cooperates with means (33,34) for retaining the slide on the head of the screw. The slide may be formed by a thin platelet (22*a*) which is provided with lateral flanges (25) and is slidable in a complementary cavity (18) provided in the plate (1) while being flush with the surface of the plate (1). The plate (1) includes ramps (26) for retaining the slide (22) on which the flanges (25) are slidable, the slide (22) being slidable to a position in which it at least partly overlaps the heads of the associated screws (6 or 7) and is locked in position by suitable means.

21 Claims, 4 Drawing Sheets

U.S. PATENT DOCUMENTS

| | | | |
|---|---|---|---|
| 2,486,303 A | * | 10/1949 | Longfellow .................... 606/71 |
| 3,386,437 A | | 6/1968 | Treace |
| 3,659,595 A | | 5/1972 | Haboush |
| 3,693,616 A | | 9/1972 | Roaf et al. |
| 3,741,205 A | | 6/1973 | Markolf et al. |
| 3,779,240 A | | 12/1973 | Kondo |
| 3,842,825 A | | 10/1974 | Wagner |
| RE28,841 E | | 6/1976 | Allgower et al. |
| 4,102,339 A | | 7/1978 | Weber et al. |
| 4,119,092 A | | 10/1978 | Gil |
| 4,408,601 A | | 10/1983 | Wenk |
| 4,484,570 A | | 11/1984 | Sutter et al. |
| 4,488,543 A | | 12/1984 | Tornier |
| 4,493,317 A | | 1/1985 | Klaue |
| 4,503,848 A | | 3/1985 | Caspar et al. |
| 4,513,744 A | | 4/1985 | Klaue |
| 4,570,624 A | | 2/1986 | Wu |
| 4,794,918 A | | 1/1989 | Wolter |
| 4,907,577 A | | 3/1990 | Wu |
| 4,911,153 A | | 3/1990 | Border |
| 4,957,496 A | | 9/1990 | Schmidt |
| 4,957,497 A | | 9/1990 | Hoogland et al. |
| 4,959,065 A | | 9/1990 | Arnett et al. |
| 5,006,120 A | * | 4/1991 | Carter ............................ 606/71 |
| 5,037,439 A | * | 8/1991 | Albrektsson et al. ........ 623/20.3 |
| 5,041,113 A | | 8/1991 | Biedermann et al. |
| 5,041,116 A | | 8/1991 | Wilson |
| 5,057,111 A | | 10/1991 | Park |
| 5,108,395 A | | 4/1992 | Laurain |
| 5,127,912 A | | 7/1992 | Ray et al. |
| 5,127,914 A | | 7/1992 | Calderale et al. |
| 5,129,899 A | | 7/1992 | Small et al. |
| 5,139,498 A | * | 8/1992 | Astudillo Ley ............... 606/281 |
| 5,147,361 A | | 9/1992 | Ojima et al. |
| 5,180,381 A | | 1/1993 | Aust et al. |
| 5,261,910 A | | 11/1993 | Warden et al. |
| 5,300,073 A | | 4/1994 | Ray et al. |
| 5,324,290 A | | 6/1994 | Zdeblick et al. |
| 5,364,399 A | | 11/1994 | Lowery et al. |
| 5,380,328 A | | 1/1995 | Morgan |
| 5,397,363 A | | 3/1995 | Gelbard |
| 5,423,826 A | | 6/1995 | Coates et al. |
| 5,484,439 A | | 1/1996 | Olson et al. |
| 5,486,176 A | | 1/1996 | Hildebrand et al. |
| 5,487,743 A | | 1/1996 | Laurain et al. |
| 5,492,442 A | | 2/1996 | Lasner |
| 5,545,166 A | | 8/1996 | Howland |
| 5,549,612 A | * | 8/1996 | Yapp et al. ..................... 606/293 |
| 5,558,674 A | | 9/1996 | Heggeness et al. |
| 5,578,034 A | | 11/1996 | Estes |
| 5,601,553 A | | 2/1997 | Trebing et al. |
| 5,607,426 A | | 3/1997 | Ralph et al. |
| 5,616,142 A | | 4/1997 | Yuan et al. |
| 5,616,144 A | | 4/1997 | Yapp et al. |
| 5,620,443 A | | 4/1997 | Gertzbein et al. |
| 5,676,666 A | | 10/1997 | Oxland et al. |
| 5,681,311 A | | 10/1997 | Foley et al. |
| 5,735,850 A | | 4/1998 | Baumgartner et al. |
| 5,766,254 A | | 6/1998 | Gelbard |
| 5,797,911 A | | 8/1998 | Sherman et al. |
| 5,800,433 A | | 9/1998 | Benzel et al. |
| 5,824,088 A | | 10/1998 | Kirsch |
| 5,827,286 A | | 10/1998 | Incavo et al. |
| 5,851,207 A | | 12/1998 | Cesarone |
| 5,876,402 A | | 3/1999 | Errico et al. |
| 5,904,683 A | | 5/1999 | Pohndorf et al. |
| 5,951,558 A | | 9/1999 | Fiz |
| 5,954,722 A | | 9/1999 | Bono |
| 5,957,927 A | | 9/1999 | Magee et al. |
| 5,964,761 A | | 10/1999 | Kambin |
| 5,973,223 A | | 10/1999 | Tellman et al. |
| 5,984,925 A | | 11/1999 | Apgar |
| 6,017,345 A | | 1/2000 | Richelsoph |
| 6,129,730 A | | 10/2000 | Bono et al. |
| 6,136,002 A | | 10/2000 | Shih et al. |
| 6,139,550 A | | 10/2000 | Michelson |
| 6,152,927 A | | 11/2000 | Farris et al. |
| 6,193,721 B1 | | 2/2001 | Michelson |
| 6,224,602 B1 | | 5/2001 | Hayes |
| 6,235,034 B1 | * | 5/2001 | Bray ................................ 606/71 |
| 6,248,105 B1 | | 6/2001 | Schlapfer et al. |
| 6,258,089 B1 | | 7/2001 | Campbell et al. |
| 6,273,889 B1 | | 8/2001 | Richelsoph |
| 6,306,136 B1 | | 10/2001 | Baccelli |
| 6,306,139 B1 | * | 10/2001 | Fuentes ........................... 606/70 |
| 6,503,250 B2 | * | 1/2003 | Paul ............................... 606/279 |
| 6,533,786 B1 | * | 3/2003 | Needham et al. ............. 606/282 |
| 6,602,256 B1 | | 8/2003 | Hayes |
| 6,652,525 B1 | | 11/2003 | Assaker et al. |
| 2002/0120273 A1 | | 8/2002 | Needham et al. |
| 2004/0158246 A1 | | 8/2004 | Assaker et al. |
| 2004/0220571 A1 | | 11/2004 | Assaker et al. |

FOREIGN PATENT DOCUMENTS

| | | |
|---|---|---|
| CH | 462375 | 9/1968 |
| CH | 468824 | 2/1969 |
| CH | 566767 | 9/1975 |
| CH | 600862 | 6/1978 |
| CH | 611147 | 5/1979 |
| CH | 613616 | 10/1979 |
| CH | 613858 | 10/1979 |
| DE | 2340880 | 4/1975 |
| DE | 4409833 A1 | 10/1995 |
| DE | 19720782 | 11/1998 |
| EP | 0016338 A1 | 10/1980 |
| EP | 0382256 | 8/1990 |
| EP | 0455255 A1 | 11/1991 |
| EP | 0599640 A1 | 6/1994 |
| EP | 0705572 A2 | 4/1996 |
| EP | 0897697 A1 | 2/1999 |
| FR | 1505513 | 12/1967 |
| FR | 2233973 | 1/1975 |
| FR | 2480106 | 10/1981 |
| FR | 2740321 | 10/1995 |
| FR | 2778088 | 11/1999 |
| GB | 780652 | 8/1957 |
| GB | 1153090 | 5/1969 |
| GB | 1601383 | 10/1981 |
| WO | 94/17744 | 8/1994 |
| WO | 95/25474 | 9/1995 |
| WO | 9834553 | 8/1998 |
| WO | 9834556 | 8/1998 |
| WO | 99/04718 | 2/1999 |
| WO | 98/52482 | 11/1999 |
| WO | 99/56653 | 11/1999 |
| WO | 01/26566 | 4/2001 |

OTHER PUBLICATIONS

Medtronic's Reply and Counterclaim (Dec. 3, 2003), *Cross Medical Products, Inc. v. Medtronic Sofamor Danek, Inc. et al.*, No. SACV 8:03-0110 GLT (C.D. Cal. filed Feb. 4, 2003).

Blackstone Anterior Cervical Plate Brochure; Blackstone Medical Inc.

Lowery, L. Gary, "Orion Anterior Cervical Plate System," 1995, pp. 1-25.

Casper, "Anterior Cervical Fusion Instrumentation and Trapezial Osteosynthetic Plates," Aesculap; Publication date unknown.

Codman, "Codman Anterior Cervical Plate System" Publication date unknown.

Spine Tech, "Cervi-Lok Cervical Fixation System Surgical Technique Manual" Publication date unknown.

Satomi, Keichi, DDS et al., "Bone-implant interface structures after nontapping and tapping insertion of scre-type titanium alloy endosseous implants," The Journal of Prothetic Dentistry, Mar. 1988 59(3):339-342.

Philips, John H. et al., "Comparison of Compression and Torque Measurements of Self-Tapping and Pretapped Screws," Plastic and Reconstructive Surgery, Mar. 1989 83(3):447-456.

An, Howard S. et al., "Spinal Instrumentation," Williams & Wilkins, 1992, pp. 1-11, 49-60, 167-196, 257-280, 379-411.

Scient'x, "Cervical Plate-Cage Systems" Publication date unknown.

Synthes, "Cervical Spine Locking Plate," 1995.

Smith & Nephew Orthopaedics, "The Aline Anterior Cervical Plate," Publication date unknown.

AcroMed, "AcroPlate Anterior Cervical System," 1994.

Author Unknown, "Dynamic Compression Plate," pp. 78-79, Publication date unknown.

Bagby, George W. et al., "An Impacting Bone Plate," from Staff Meetings of the Mayo Clinic, Feb. 6, 1957, 32 (3):55-57.

Bagby, George W. et al., "The Effect of Compression of the Rate of Fracture Healing using a Special Plate," American Journal of Surgery, May 1958, 95:761-771.

Bertolin, "The Use of My Compression Plate for Osteosystheses of the Various Types of Femoral Intertrochanteric Osteotomies," Translation from Italian of a paper presented at the Congress of the Society of Orthopaedics and Traumatology fo the Medical Union of the Latin Mediterranean, Jun. 6-7, 1965.

"Premier™ Anterior Cervical Plate System Surgical Technique," Medtronic Sofamor Danek © 2000.

"Zephir™ Anterior Cervical Plate System Surgical Technique," Medtronic Sofamor Danek © 2000.

Order on (1) Cross-Motions for Partial Summary Judgment re: Invalidity of the '602 Patent; (2) Plaintiffs Motion for Partial Summary Judgment re: Infringement of the '602 Patent, *Cross Medical Products, Inc. v. Medtronic Sofamor Danek, Inc., et al.*, Case No. SA CV 03-110-GLT (ANx) (C.D. Cal. filed Feb. 4, 2003).

Order on (1) Cross-Motions for Partial Summary Judgment re: Infringement of the '786 Patent; (2) Cross-Motions for Partial Summary Judgment re: Invalidity and Unednforceability of the '786 Patent, *Cross Medical Products, Inc. v. Medtronic Sofamor Danek, Inc., et al.*, Case No. SA CV 03-110-GLT (ANx) (C.D. Cal. filed Feb. 4, 2003).

Denis J. Diangelo et al., "Cervical Plating Systems Reverse Load Transfer Through Multi-Level Strut-Grafts," North American Congress on Biomechanics, University of Waterloo, Waterloo, Ontario, Canada, 3 pages (Aug. 14-18, 1998).

510(k) Summary of Safety and Effectiveness in Accordance with SMDA of 1990 Aesculap ABS Cervical Plating System, U.S. Food and Drug Administration, 6 pages, Submitted Dec. 15, 1997.

Peak Fixation System, Polyaxial Cervical Plate, 20 pages, © 1998 DePuy Motech, Inc.

Kevin T. Foley et al., Abstract of "Anterior Cervical Plating Reverses Load Transfer Through Multi-Level Strut-Grafts," Congress of Neurological Surgeons, Seattle Washington 1998.

Kevin T. Foley et al., Abstract of "Anterior Cervical Plating Does Not Prevent Strut Graft Displacement in Multilevel Cervical Corpectomy," Congress of Neurological Surgeons, AANS 1997 Denver.

Christopher G. Paramore et al., "Radiographic and Clinical Follow-Up Review of Caspar Plates in 49 Patients," 84 J. Neurosurg. 957-961 (1996).

Limited. (n.d.) The American Heritage® Dictionary of the English Language, Fourth Edition. Retrieved Mar. 18, 2007, from Dictionary.com website: http://dictionary.reference.com/browse/limited.

Cross' Reply Brief in Support of Its Cross-Motion for Partial Summary Judgment of No Invalidity and No Unenforceability of U.S. Patent No. 6,224,602 (filed Dec. 6, 2004), *Cross Medical Products, Inc. v. Medtronic Sofamor Danek, Inc., et al.*, including Case No. SACV 03-110 GLT (ANx) (C.D. Cal. filed Feb. 4, 2003).

Cross Medical Products, Inc.'s Notice of Motion and Motion for Partial Summary Judgment of Defendants' Affirmative Defense of Invalidity, Counterclaim of Invalidity, and Other Affirmative Defenses Regarding U.S. Patent No. 6,224,602 (filed Nov. 3, 2004), *Cross Medical Products, Inc. v. Medtronic Sofamor Danek, Inc., et al.*, including Case No. SACV 03-110 GLT (ANx) (C.D. Cal. filed Feb. 4, 2003).

Defendants and Counterclaimants Medtronic Sofamor Danek, Inc. and Medtronic Sofamor Danek USA, Inc., and Counterclaimant SDGI Holdings, Inc's Memorandum of Points and Authorities in Support of Its Motion for Partial Summary Judgment of Invalidity of U.S. Patent No. 6,224,602 (filed Oct. 14, 2004), *Cross Medical Products, Inc. v. Medtronic Sofamor Danek, Inc., et al.*, Case No. SACV 03-110 GLT (ANx)(C.D. Cal. filed Feb. 4, 2003).

Defendants and Counterclaimants Medtronic Sofamor Danek, Inc. and Medtronic Sofamor Danek USA, Inc., and Counterclaimant SDGI Holdings, Inc's Statement of Uncontroverted Facts and Conclusions of Law in Support of Its Motion for Partial Summary Judgment of Invalidity of U.S. Patent No. 6,224,602 (filed Oct. 14, 2004), *Cross Medical Products, Inc. v. Medtronic Sofamor Danek, Inc., et al.*, Case No. SACV 03-110 GLT (ANx)(C.D. Cal. filed Feb. 4, 2003).

Declaration of Stephanie J. Kravetz in Support of Defendants' and Counterclaimants' Motion for Partial Summary Judgment of Invalidity of U.S. Patent No. 6,224,602 (filed Oct. 14, 2004), *Cross Medical Products, Inc. v. Medtronic Sofamor Danek, Inc., et al.*, including Exhibits 1-39, Case No. SACV 03-110 GLT (ANx)(C.D. Cal. filed Feb. 4, 2003).

Defendants and Counterclaimants Medtronic Sofamor Danek, Inc. et al.'s Statement of Genuine Factual Issues and Disputed Conclusions of Law in Opposition to Cross's Cross-Motion for Partial Summary Judgment of No Validity and No Unenforceability of U.S. Patent No. 6,224,602 (filed Nov. 19, 2004), *Cross Medical Products, Inc. v. Medtronic Sofamor Danek, Inc., et al.*, Case No. SACV 03-110 GLT (ANx)(C.D. Cal. filed Feb. 4, 2003).

Defendants' and Counterclaimants' Memorandum of Law: (1) in Reply to Plantiff's Opposition to Motion for Summary Judgment of Invalidity, and (2) In Opposition to Plaintiff's Counter-Motion for Partial Summary Judgment of No Invalidity and No Unenforceability of U.S. Patent No. 6,224,602 (filed Nov. 19, 2004), *Cross Medical Products, Inc. v. Medtronic Sofamor Danek, Inc., et al.*, Case No. SACV 03-110 GLT (ANx)(C.D. Cal. filed Feb. 4, 2003).

Declaration of Robert A. Auchter in Support of Defendants and Counterclaimants Medtronic Sofamor Danek, Inc. and Medtronic Sofamor Danek USA, Inc.'s Memorandum of Points and Authorities in Opposition to Cross's Cross-Motion for Partial Summary Judgment of No Invalidity and No Unenforceability of U.S. Patent No. 6,224,602 (filed Nov. 19, 2004), *Cross Medical Products, Inc. v. Medtronic Sofamor Danek, Inc., et al.*, including Exhibits 1-7, Case No. SACV 03-110 GLT (ANx)(C.D. Cal. filed Feb. 4, 2003).

Cross's Memorandum of Points and Authorities (1) In Opposition to Medtronic's Motion for Partial Summary Judgment of Invalidity of U.S. Patent No. 6,224,602 , and (2) In support of It's Cross-Motion for Partial Summary of No Invalidity and No Unenforceability of U.S. Patent No. 6,224,602 (filed Nov. 3, 2004), *Cross Medical Products, Inc. v. Medtronic Sofamor Danek, Inc., et al.*, including Exhibits 1-7, Case No. SACV 03-110 GLT (ANx)(C.D. Cal. filed Feb. 4, 2003).

Plaintiff and Counterclaim Defendant Cross Medical Products, Inc.'s Genuine Issue of Material Fact In Opposition to Defendants and Counterclaimants Medtronic Sofamor Danek, Inc. and Medtronic Sofamor Danek USA, Inc. and Counter-Claimant SDGI Holdings, Inc.'s Statement of Uncontroverted Facts and Conclusions of Law in Support of Its Motion for Partial Summary Judgment of Invalidity of U.S. Patent No. 6,224,602 (filed Nov. 3, 2004), *Cross Medical Products, Inc. v. Medtronic Sofamor Danek, Inc., et al.*, including Exhibits 1-7, Case No. SACV 03-110 GLT.

Cross Medical Products, Inc.'s Statement of Uncontroverted Facts and Conclusion of Law In Support of Its Motion for Partial Summary Judgment of No Invalidity and No Unenforceability of U.S. Patent No. 6,224,602 (Nov. 3, 2004), *Cross Medical Products, Inc. v. Medtronic Sofamor Danek, Inc., et al.*, Case No. SACV 03-110 GLT (ANx) (C.D. Cal. filed Feb. 4, 2003).

Declaratin of Mark A. Finkelstein (1) In Opposition to Medtronic's Motion for Partial Summary Judgment of Invalidity of U.S. Patent No. 6,224,602, and (2) In Support of Its Cross-Motion for Partial Summary Judgment of No Invalidity and No Unenforceability of U.S. Patent 6, 224,602 (Nov. 1, 2004), *Cross Medical Products, Inc. v. Medtronic Sofamor Danek, Inc., et al.*, including Case No. SACV 03-110 GLT (ANx) (C.D. Cal. filed Feb. 4, 2003).

* cited by examiner

ANTERIOR IMPLANT FOR THE SPINE

CROSS-REFERENCE TO RELATED APPLICATIONS

The present application is a continuation of U.S. application Ser. No. 10/693,604, filed Oct. 27, 2003, which is a continuation of U.S. application Ser. No. 09/692,894, filed Oct. 20, 2000, now U.S. Pat. No. 6,652,525, which is a continuation of International Patent Application Number PCT/IB99/00794, filed Apr. 30, 1999, all of which are hereby incorporated by reference in their entirety.

TECHNICAL FIELD

The present invention relates to an implant for the spine, and more particularly, but not exclusively relates to an anterior plate for maintaining a bone graft, bone anchorage screws for the plate and means for blocking the screws and preventing any migration of the latter.

BACKGROUND

Spinal plates may be introduced from the anterior to stabilize the cervical spine and maintain in position or secure a bone graft which fills the spaces left by the extraction of at least one vertebral disc and, possibly, part of a contiguous cervical vertebra.

The bone anchorage screws used for fixing this type of plate in position are either unicortical, and therefore short, since they pass through only the anterior cortical of the vertebra, or bicortical, and therefore long, since they extend through the anterior cortical and the posterior cortical. The short unicortical screws utilize a locking element when there is a possibility the screws may back-out. On the other hand, the long bicortical screws, while less likely to unscrew, have other limitations making them less desirable in certain situations.

In practice, the locking element employed up to the present time for unicortical screws is an additional screw which is positioned between two bone anchorage screws and whose head overlaps the heads of these two screws. While there are thin cervical plates without a locking element, the addition of an existing locking element to a given plate design typically results in an increase in plate size, such as the plate's thickness. These additions may also result in a greater plate width than is desirable. Thus, the general desire to further decrease the size of surgical implants indicates a need for new plate and/or locking element arrangements.

DISCLOSURE OF THE INVENTION

Accordingly, one object of the present invention is to provide a unique device for stabilizing a patient's spine.

Additionally or alternatively, another object of the invention is to provide an anterior cervical plate provided with antimigration means for the screws arranged in such manner as to avoid increasing the overall size of the plate.

One form of the present invention is a unique device for stabilizing a patient's spine. In a further form, a slide is incorporated into a spinal plate that may be operable to serve as a locking element.

According to another form of the invention, a plate has means for blocking the bone anchorage screws that comprises at least one slide slidably mounted on the plate so as to be capable of partially covering at least one anchorage screw head, and the slide cooperates with means for retaining it on the head of the screw.

In still another form, the slide is formed by a thin platelet provided with at least one flange and slidable in a complementary cavity provided on the surface of the plate, the cavity having a ramp on which the flange can be engaged; the retaining means are formed by a boss on the plate which clicks into an associated recess when the slide is in its position for blocking and locking the screw. The cavity and the platelet may be so dimensioned that the surface of the platelet is flush with that of the plate when it is placed in its cavity. Consequently, for this form, the overall thickness of the anterior plate may not be increased by the slide.

Further forms, embodiments, objects, aspects and features of the invention will be apparent from the following description and the accompanying drawings.

MODE(S) FOR CARRYING OUT THE INVENTION

For the purposes of promoting an understanding of the principles of the invention, reference will now be made to the embodiments illustrated in the drawings and specific language will be used to describe the same. It will nevertheless be understood that no limitation of the scope of the invention is intended. Any alterations and further modifications in the illustrated or described embodiments, and any further applications of the principles of the invention as described or illustrated therein being contemplated as would normally occur to one skilled in the art to which the invention relates.

Figure 1:
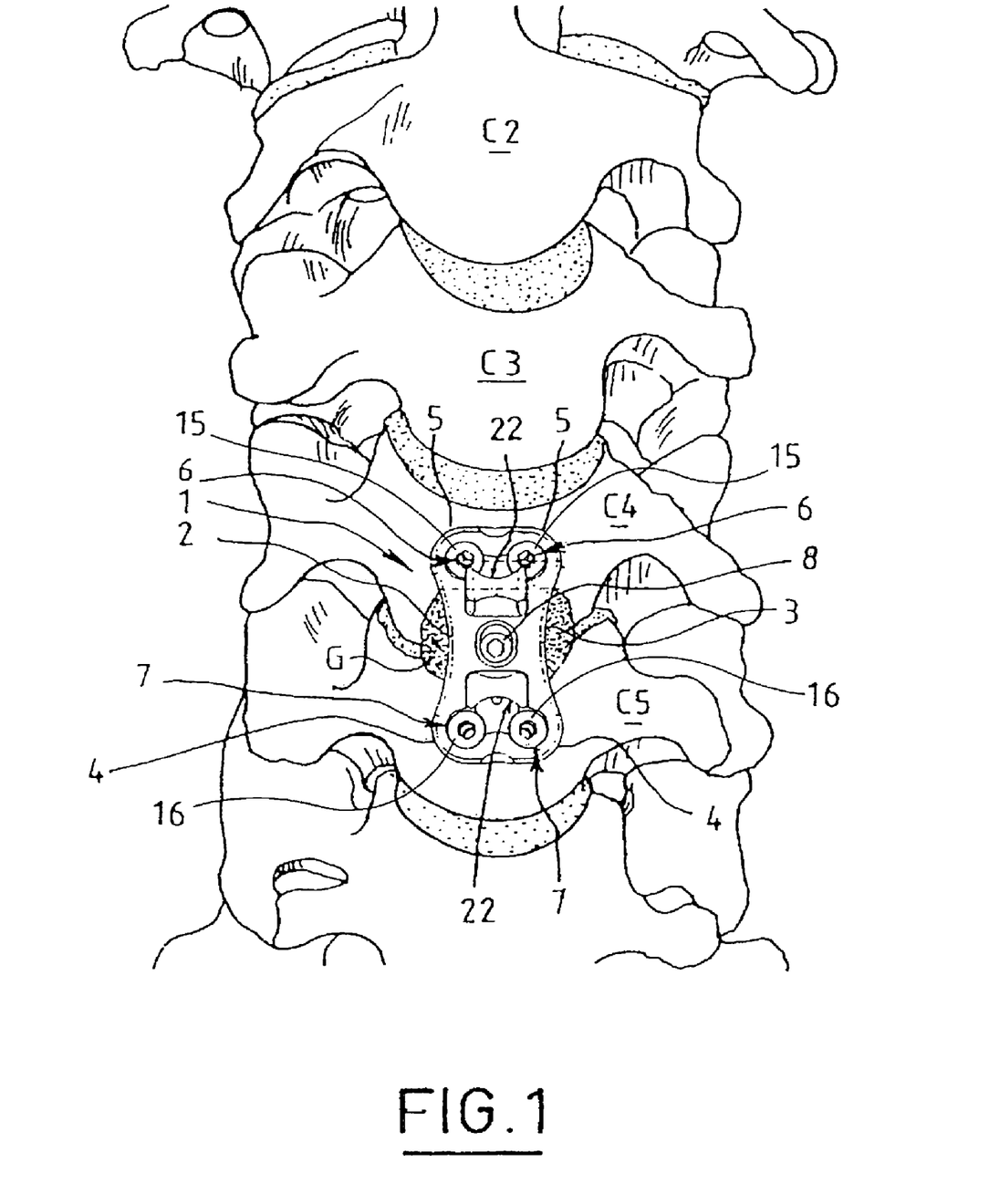
FIG. 1 is an elevation view of a cervical spine segment provided with an anterior implant according to the invention for maintaining a bone graft in position.

Shown in FIG. 1 is a cervical spine segment C2, C3, C4, C5, and between the vertebrae C4 and C5 (more usually C4 and C5) of which a bone graft G (partially visible) is disposed, this graft G being covered by an anterior plate 1 whose function is to stabilize the spine and to maintain this bone graft G in position.

Figure 2:
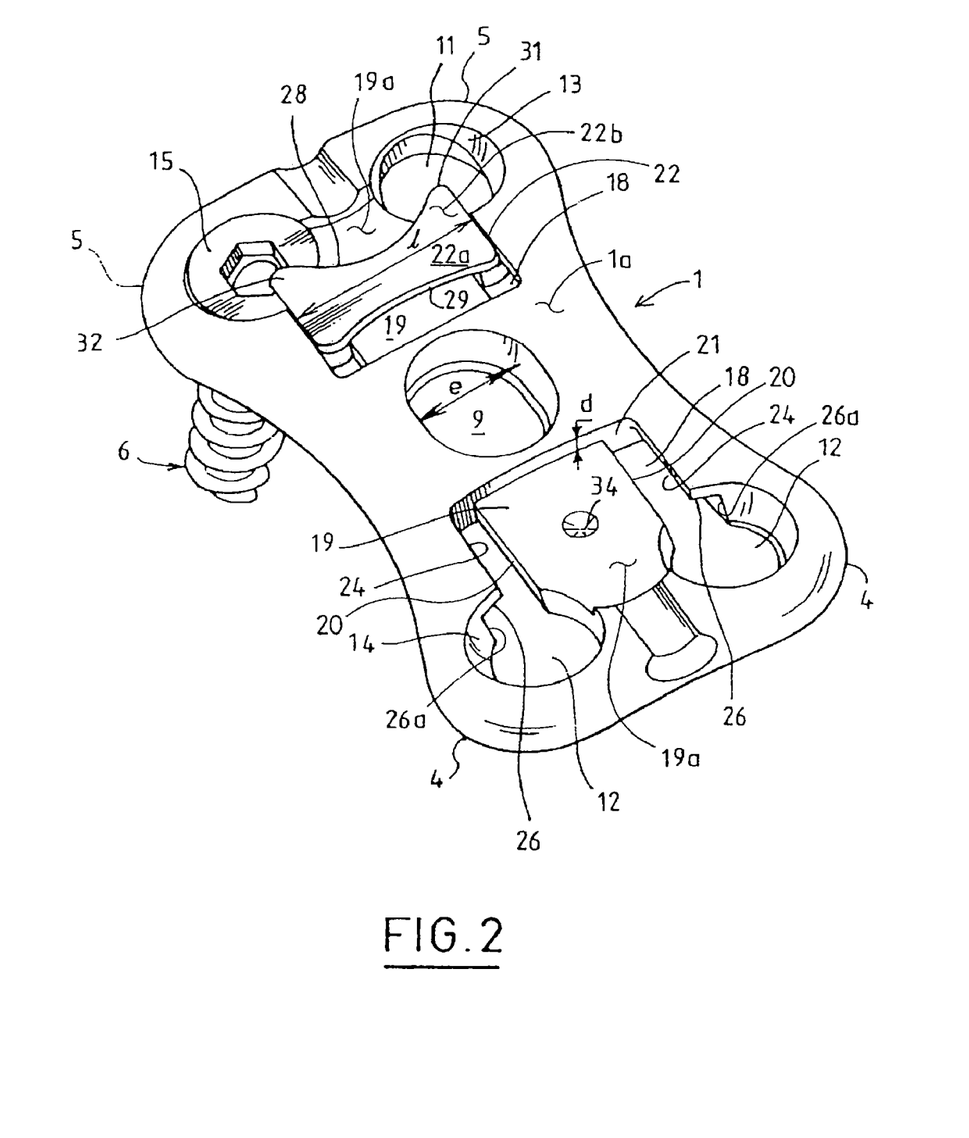
FIG. 2 is a perspective view, to a larger scale, of the anterior plate of FIG. 1 provided with a slide for locking two of the screws of the plate.

Referring additionally to FIG. 2, the plate 1 has an elongate shape with two large concave sides 2, 3 connected to rounded ends 4, 5, these large sides 2, 3 extend from the vertebra C4 to the vertebra C5. The plate 1 is provided adjacent to each of its ends 4, 5 with a pair of bone anchorage screws 6, 7 at C4 and C5 which are unicortical and therefore short, and a central screw 8 which is engaged in an oblong opening 9. Each of the screws 6, 7 extends through a corresponding opening 11, 12 which is of generally circular section but has a spherical wall 13, 14 acting as a bearing surface for the corresponding head 15, 16 of screws 6, 7.

Each pair of openings 11 and 12 opens onto a respective cavity 18 provided in the adjacent surface 1a of the plate 1. Formed in this cavity 18, which in the presently-described embodiment opens onto the opposite faces of the plate 1, is a bridge 19 which defines at one end a part of the circumference of the openings 11,12 and extends from the latter to the opposite wall 21 of the cavity 18. However, the thickness of each bridge 19 is less than that of the plate 1 so that the surface 19a of each bridge 19 is situated within the cavity 18 at a distance d from the surface 1a of the plate 1 (FIG. 2).

Figure 3:
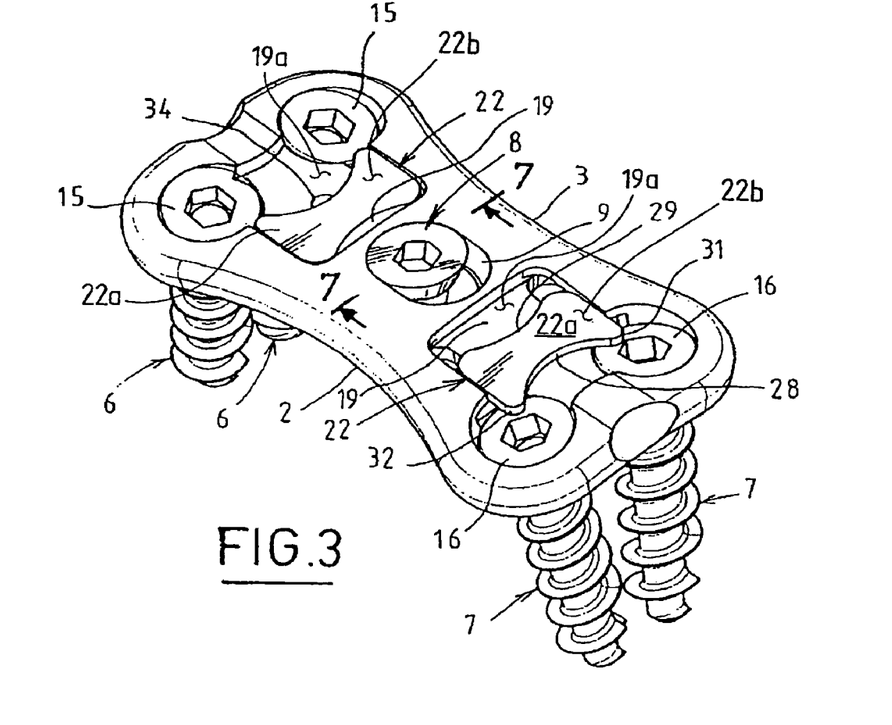
FIG. 3 is a perspective view, similar to FIG. 2, showing the plate provided with two slides and two pairs of bone anchorage screws.
Figure 4:
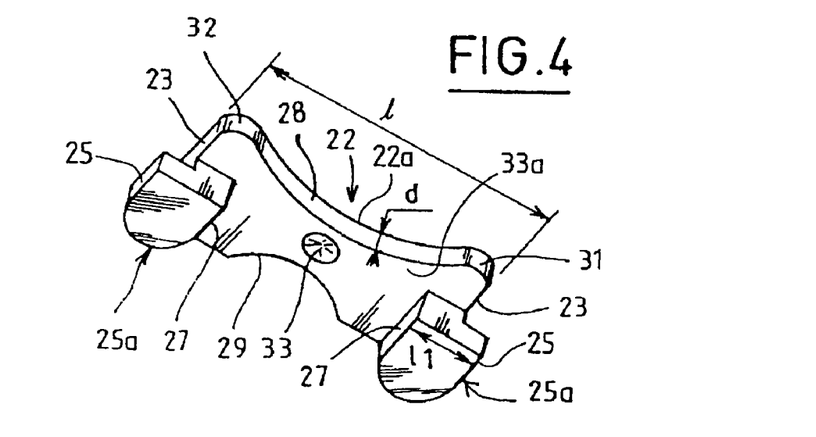
FIG. 4 is a bottom perspective view, to a larger scale, of one of the screw-blocking slides for the anterior plate of FIGS. 1-3.

Each pair of bone anchorage screws 6, and each pair of screws 7, is associated with a slide 22 for locking screws 6, 7 after anchorage in the vertebral bodies C4, C5, respectively; and thereby preventing migration of the screws 6, 7. Referring further to FIGS. 3 and 4, each slide 22 is formed by a thin platelet 22a whose thickness is at the most about equal to the distance d between the upper surface 1a of the plate 1 and the surface 19a of the bridge 19. This platelet 22a has an elongate shape whose larger dimension l is just equal to the width of the cavity 18 to allow insertion of the platelet 22a in the latter. Each platelet 22a, not cambered in the free state, is generally slightly cambered in order to make it possible to insert it into its housing cavity 18.

Figures 5, 6, 7:
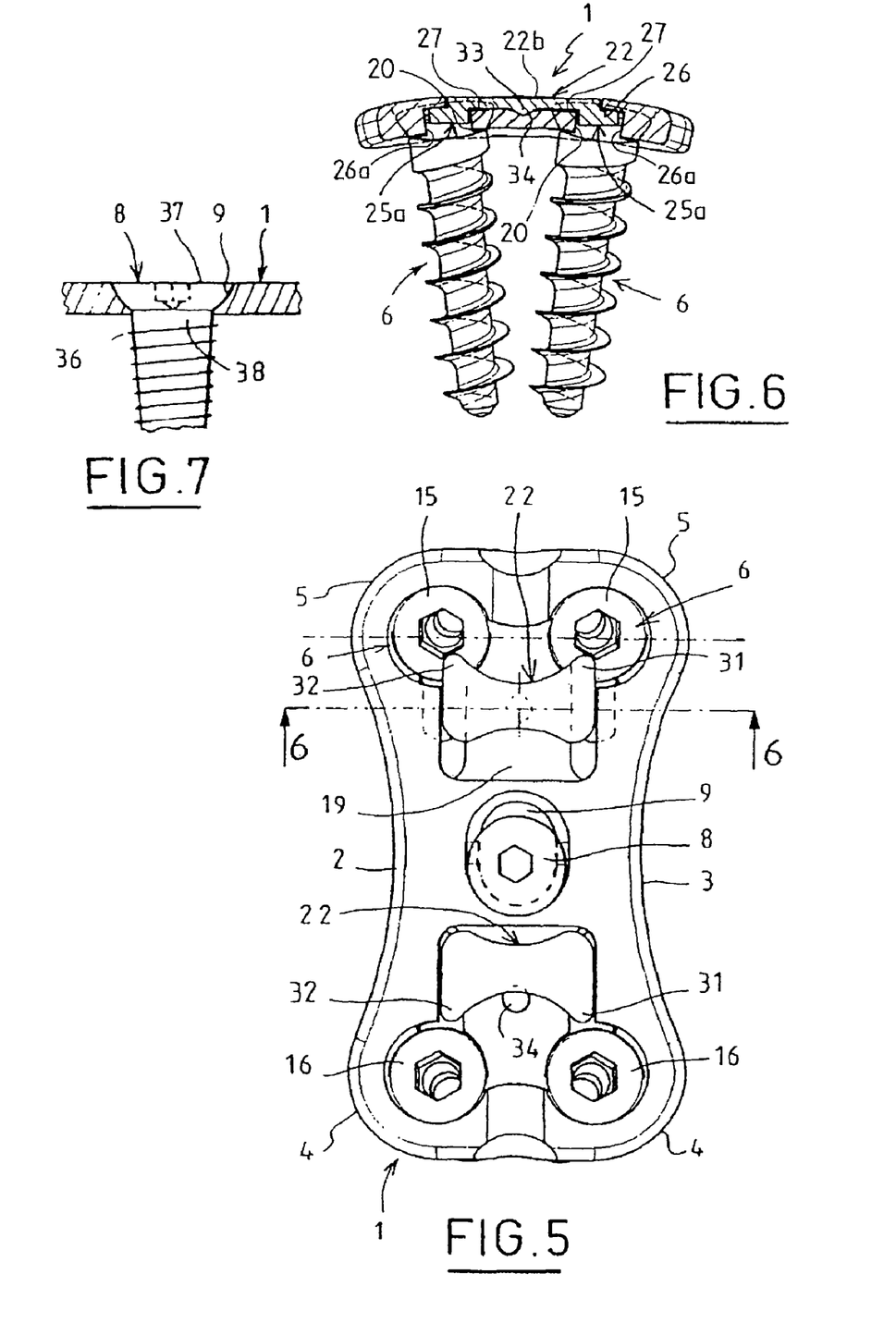
FIG. 5 is a top view to a larger scale of the anterior plate of FIGS. 1-3 provided with two screw locking slides, one of these slides being in the locking position, while the other is in the withdrawn position before locking.
FIG. 6 is a cross-sectional view taken on line 6-6 of FIG. 5.
FIG. 7 is a partial cross-sectional view taken on line 7-7 of FIG. 3.

This insertion is carried out by positioning it on the bridge 19 and applying a force such that its opposite sides 23 slidably and resiliently bear against the retaining ramps 26. Retaining ramps 26 are each defined along a corresponding one of the opposite sides 24 of cavity 18. Further, each platelet 22a is provided with two lateral flanges 25 which project from the sides 23 under the central part of the platelet 22a. Each of the flanges 25 is adapted to form a shoe 25a slidable along a respective retaining ramp 26 (FIGS. 2 and 6). The flanges 25 have a width l allowing their insertion in the slots 26a between the sides 24 of the cavity 18 and the opposing sides 20 of the bridge 19, so that their inner faces 27 are placed in sliding contact with the sides 20 of the bridge 19 (FIG. 6) when the platelet 22a has been placed in position.

The two large sides 28, 29 of each platelet 22a are concave and the apices 31, 32 of each platelet 22a are rounded so that the rounded apices 31, 32 of the sides 28 close to the screws 6 or 7 are able to partly overlap the heads 15, 16 of the screws 6, 7 when the platelets 22a are in position for locking the screws 6, 7 (FIGS. 1, 2, 5, 6). Indeed, the openings 11, 12 and the heads 15, 16 are so arranged that, when the screws 6, 7 have been screwed into the vertebral bodies with possibly an inclination in regard to plate 1, their heads 15, 16 have their surfaces in a position in which they are just flush with the underside of the round apices 31, 32.

Referring more specifically to FIGS. 2-6, means are provided for retaining the platelets 22a in their position for locking the screws 6, 7. In the presently-described embodiment, these means comprise, for each platelet 22a, a central boss 33 projecting from the lower face 33a of the platelet 22a, namely that placed in contact with the surface 19a of the support bridge 19, and a corresponding recess 34 provided in the central part of the bridge 19. Thus, when the platelet 22a reaches the position for locking the screws 6, 7; its boss 33 clicks into the recess 34 and maintains the platelet 22a in this position and prevents it from moving forwardly or rearwardly in its cavity 18.

Referring next to FIGS. 2, 3, 5, and 7, the first thread 36 of the central screw 8 (i.e., the thread closest to its head 37, See FIG. 7) is separated from the latter by a smooth part 38. The diameter of this first thread 36 is larger than that of the smooth part 38 and the width e of the oblong opening 9 arranged to receive screw 8 (See FIG. 2). To place the screw 8 in position, it is therefore necessary to force it through the opening 9 and cause the latter to pass beyond the first thread 36. Thereafter, the latter performs the function of means for retaining screw 8 in plate 1.

To place the plate 1 and its locking slides 22 in position on the cervical segment such as C4, C5 of FIG. 1, the procedure is the following. Referring generally to FIGS. 1-7, first of all, after the bone graft G has been placed in position in the discal space previously prepared, the surgeon positions the plate 1 equipped with slides 22 and attaches it by means of screws 6 and 7. Afterwards he makes each slide 22 run from the bottom of its housing cavity 18 until flanges 25 come and stop against screws heads 15 and 16. The latter are then partially covered by rounded tops 31, 32 as shown in FIGS. 1, 2, 3, and 5 for at least one of slides 22. When the slides 22 reach this position, in which they partly overlap the heads 15, 16; their respective boss 33 clicks into the respective recess 34 so that each slide 22 is locked in this position in which it locks the associated screws 15, 16 against any migration and therefore against any posterior movement.

As can be seen in FIG. 6, the slides 22 do not project above the surface of the plate 1 owing to their small thickness which is at the maximum equal to about d and to the provision of a suitable cavity 18. Thus the surface 22b of the slides 22 is generally flush with surface 1a of the plate 1 whose overall thickness is consequently not increased by the presence of the locking slides 22. The locking platelets 22a do not impose to increase the width of the plate 1 in respect to its minimum width such that the same results from the chosen gap between the axis of screws 6 and 7.

It should be appreciated that the scope of the invention is not intended to be limited to the described embodiments and may encompass variants. For example, boss 33 can be formed on support 19 whilst recess 34 is formed on the platelet 22a. Thus the means 33, 34 for blocking the slides 22 in their locking position may be replaced by any other like system. Further, in another arrangement, a slide is associated with each screw and has a single flange that is suitably dimensioned for this purpose. Optionally, the plate may be provided with only a single blocking slide 22, the second pair of screws being for example associated with other blocking means, or being absent. Moreover, in further embodiments, the implant according to the invention can be used, not only for the cervical spine, but also for other spine segments, for example thoracic and lumbar, and possibly without any bone grafts. Further, in other embodiments, the screw-locking slide and plate arrangement may be used to reduce undesired migration of one or more screws of a type other than the unicortical variety; and may be used to check undesired migration of other types of fasteners used in addition to or as an alternative to one or more screws.

In one alternative embodiment of the present invention, an implant for the spine includes an anterior plate for stabilizing the spine and maintaining a bone graft that has a number of openings, a number of bone anchorage screws for correspondingly engaging the openings of the plate, and means for blocking the screws and preventing any migration of the screws. This implant is further characterized in that the blocking means comprises at least one slide slidably mounted on the plate so as to be capable of partially covering at least one anchorage screw head. This slide cooperates with means for retaining the slide on the head of the screw.

In further embodiment, an implant for the spine includes: a plate for stabilizing the spine that has a number of openings; a number of bone anchorage screws each operable to engage a corresponding one of the openings of the plate; and means for blocking the screws and preventing screw migration. The blocking means includes at least one slide slidably mounted on the plate to selectively cover at least a part of at least one of the screws and means for retaining the slide on at least one of the screws.

In an additional embodiment, an implant for the spine includes: a plate for stabilizing the spine that comprises a number of openings and defines a cavity adjacent at least one of the openings; a number of bone anchorage screws each operable to pass through a corresponding one of the openings of the plate to engage the spine; and a slide slidably mounted in the cavity of the plate. The slide is operable to selectively cover at least a portion of at least one of the screws mounted in at least one of the openings.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An implant for the spine, comprising:
   a plate for engaging the spine, the plate having front and back surfaces and a plurality of fixation openings extending between the front and back surfaces, wherein the back surface is adapted to contact the spine;
   a plurality of bone anchorage screws, each operable to extend through a corresponding fixation opening of the plate;
   a plurality of cavities formed in the front surface of the plate, each of which is in communication with a corresponding fixation opening; and
   a plurality of locking slides, each configured to be positioned in a corresponding one of the cavities,
   wherein the locking slides are slidable between unlocked positions, in which the bone anchorage screws may be positioned through corresponding fixation openings, and locked positions, in which the bone anchorage screws are locked within the corresponding fixation openings,
   wherein each locking slide slides between the unlocked and locked positions along a path oriented in a longitudinal direction with respect to the plate, and
   wherein the plate further comprises a pair of retaining flanges for each cavity, each pair of retaining flanges retaining a corresponding locking slide in the cavity as the locking slide slides along the path.

2. The implant for the spine according to claim 1, wherein the fixation openings are provided in pairs, with the fixation openings of each pair being symmetrically positioned on opposing sides of a longitudinal axis extending along the center line of the plate.

3. The implant for the spine according to claim 2, wherein a first locking slide of the plurality of locking slides slides into the locked position in a direction opposite of that of a second locking slide of the plurality of locking slides.

4. The implant for the spine according to claim 2, wherein the plate comprises a pair of concave side edge sections, which are symmetrically positioned on opposing sides of the longitudinal axis.

5. The implant for the spine according to claim 4, wherein the concave side edge sections are positioned between adjacent pairs of fixation openings, with respect to the longitudinal axis.

6. The implant for the spine according to claim 5, wherein the corners of the plate are rounded.

7. The implant for the spine according to claim 5, wherein the plate further comprises an opening extending between the front and back surfaces of the plate, which is centrally positioned in the front surface of the plate.

8. The implant for the spine according to claim 7, wherein the locking slides have thicknesses relative to the depths of the cavities such that the locking slides are flush with the front surface of the plate when positioned in the cavities.

9. The implant for the spine according to claim 8, wherein the plate comprises four fixation openings and four bone anchorage screws.

10. The implant for the spine according to claim 1, wherein a lead edge of each locking slide, when moving from the unlocked position to the locked position, is concave.

11. The implant for the spine according to claim 10,
    wherein each locking slide further comprises a pair of lateral flanges that engage the pair of retaining flanges of the corresponding cavity, such that the locking slide is slidably retained in the cavity.

12. The implant for the spine according to claim 11, wherein the implant comprises four bone anchorage screws and four corresponding fixation openings, and
    wherein a different locking slide is provided for each fixation opening.

13. The implant for the spine according to claim 1, wherein each locking slide includes a projection which engages a corresponding recess on the plate when in the locked position so as to retain the locking slide in the locked position.

14. The implant for the spine according to claim 1, wherein each locking slide includes a recess which receives a corresponding projection on the plate when in the locked position so as to retain the locking slide in the locked position.

15. An implant for the spine, comprising:
    a plate for engaging the spine, the plate having front and back surfaces and a plurality of fixation openings extending between the front and back surfaces, wherein the back surface is adapted to contact the spine and the plurality of fixation openings are adapted to receive bone anchorage screws;
    a plurality of depressions formed on the front surface of the plate; and
    a plurality of locking slides, each configured to be positioned in a corresponding one of the depressions and to lock a bone anchorage screw within a corresponding fixation opening of the plurality of fixation openings,
    wherein each locking slide is slidable between an unlocked position, in which the bone anchorage screw may be positioned through the corresponding fixation opening, and a locked position, in which the bone anchorage screw is locked within the corresponding fixation opening,
    wherein each locking slide slides between the unlocked and locked positions along a path oriented in a longitudinal direction with respect to the plate,
    wherein the fixation openings are provided in pairs, with the fixation openings of each pair being symmetrically positioned on opposing sides of a longitudinal axis extending along the center line of the plate,
    wherein a first locking slide of the plurality of locking slides slides into the locked position in a direction opposite of that of a second locking slide of the plurality of locking slides, and
    wherein each locking slide includes a recess which is engaged by a corresponding projection on the plate when in the locked position so as to retain the locking slide in the locked position.

16. The implant for the spine according to claim 15, wherein the plate further comprises a pair of retaining flanges for each depression, and
wherein each locking slide further comprises a pair of lateral flanges that engage the pair of retaining flanges of the corresponding depression, such that the locking slide is slidably retained along the path.

17. The implant for the spine according to claim 16, wherein the implant further comprises the plurality of bone anchorage screws.

18. An implant for the spine, comprising:
a plate for engaging the spine, the plate having front and back surfaces and a plurality of fixation openings extending between the front and back surfaces, wherein the back surface is adapted to contact the spine;
a plurality of bone anchorage screws, each operable to extend through a corresponding fixation opening of the plate;
a plurality of cavities formed on the front surface of the plate; and
a plurality of locking slides, each configured to be positioned in a corresponding one of the cavities and to lock a bone anchorage screw of the plurality of bone anchorage screws within the corresponding fixation opening,
wherein each locking slide is slidable between an unlocked position, in which the bone anchorage screw may be positioned through the corresponding fixation opening, and a locked position, in which the bone anchorage screw is locked within the corresponding fixation opening,
wherein each locking slide slides between the unlocked and locked positions along a path oriented in a longitudinal direction with respect to the plate,
wherein the plate further comprises a pair of retaining flanges for each cavity, each pair of retaining flanges retaining a corresponding locking slide in the cavity as the locking slide slides along the path, and
wherein each locking slide includes a recess which receives a corresponding projection on the plate when in the locked position so as to retain the locking slide in the locked position.

19. The implant for the spine according to claim 18, wherein each locking slide further comprises a pair of lateral flanges that engage the pair of retaining flanges of the corresponding cavity, such that the locking slide is slidably retained in the cavity.

20. The implant for the spine according to claim 19, wherein the fixation openings are provided in pairs, with the fixation openings of each pair being symmetrically positioned on opposing sides of a longitudinal axis extending along the center line of the plate.

21. The implant for the spine according to claim 20, wherein a first locking slide of the plurality of locking slides slides into the locked position in a direction opposite of that of a second locking slide of the plurality of locking slides, and
wherein the plate further comprises an opening extending between the front and back surfaces of the plate, which is centrally positioned in the front surface of the plate.

* * * * *